United States Patent
Kassab

(10) Patent No.: US 9,314,169 B2
(45) Date of Patent: *Apr. 19, 2016

(54) DEVICES, SYSTEMS, AND METHODS TO DETERMINE FRACTIONAL FLOW RESERVE

(71) Applicant: 3DT Holdings, LLC, San Diego, CA (US)

(72) Inventor: Ghassan S. Kassab, La Jolla, CA (US)

(73) Assignee: 3DT Holdings, LLC, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/258,935

(22) Filed: Apr. 22, 2014

(65) Prior Publication Data

US 2014/0316289 A1 Oct. 23, 2014

Related U.S. Application Data

(63) Continuation of application No. 13/120,308, filed as application No. PCT/US2009/057800 on Sep. 22, 2009, now Pat. No. 8,702,613.

(60) Provisional application No. 61/098,837, filed on Sep. 22, 2008.

(51) Int. Cl.
*A61B 5/02* (2006.01)
*A61B 5/0215* (2006.01)
(Continued)

(52) U.S. Cl.
CPC .............. *A61B 5/02158* (2013.01); *A61B 5/026* (2013.01); *A61B 5/0275* (2013.01); *A61B 5/02007* (2013.01); *A61B 5/028* (2013.01); *A61B 5/053* (2013.01)

(58) Field of Classification Search
CPC .. A61B 5/02158; A61B 5/0275; A61B 5/026; A61B 5/053; A61B 5/02007; A61B 5/028; A61B 5/0265; A61B 5/0267
USPC .......... 600/481, 483, 485, 486, 504, 505, 507
See application file for complete search history.

(56) References Cited

U.S. PATENT DOCUMENTS

| | | |
|---|---|---|
| 3,896,373 A | 7/1975 | Zelby |
| 5,782,774 A | 7/1998 | Shmulewitz |

(Continued)

OTHER PUBLICATIONS

Siebes et al., Influence of hemodynamic conditions on fractional flow reserve: parametric analysis of underlying model, Am J Physiol Heart Circ Physiol, vol. 283, 2002, pp. H1462-H1470.

(Continued)

*Primary Examiner* — Michael Kahelin
*Assistant Examiner* — Tho Tran
(74) *Attorney, Agent, or Firm* — Reichel Stohry LLP; Mark C. Reichel; Natalie J. Dean

(57) ABSTRACT

Devices, systems, and methods to determine fractional flow reserve. At least one method for determining fractional flow reserve of the present disclosure comprises the steps positioning a device comprising at least two sensors within a luminal organ at or near a stenosis, wherein the at least two sensors are separated a predetermined distance from one another, operating the device to determine flow velocity of a second fluid introduced into me luminal organ to temporarily displace a first fluid present within the luminal organ, and determining fractional flow reserve at or near the stenosis based upon the flow velocity, a mean aortic pressure within the luminal organ, and at least one cross-sectional area at or near the stenosis. Devices and systems useful for performing such exemplary methods are also disclosed herein.

20 Claims, 9 Drawing Sheets

(51) Int. Cl.
*A61B 5/026* (2006.01)
*A61B 5/0275* (2006.01)
*A61B 5/028* (2006.01)
*A61B 5/053* (2006.01)

(56) References Cited

U.S. PATENT DOCUMENTS

| | | |
|---|---|---|
| 5,842,998 A | 12/1998 | Gopakumaran et al. |
| 2004/0230131 A1 | 11/2004 | Kassab et al. |
| 2007/0078352 A1 | 4/2007 | Pijls |
| 2007/0265687 A1 | 11/2007 | Deem et al. |
| 2008/0033316 A1 | 2/2008 | Kassab et al. |
| 2008/0119741 A1 | 5/2008 | Friedman et al. |
| 2009/0048518 A1* | 2/2009 | Furman ............... A61B 5/0031 600/454 |

OTHER PUBLICATIONS

Geddes, Cardiac Output Using the Saline-Dilution Impedance Technique, IEEE Engineering in Medicine and Biology Magazine, Mar. 1989, pp. 22-26.

Bishop et al., Fractional Flow Reserve: Critical review of an important physiologic adjunct to angiography, Am heart J, 2004, vol. 147, pp. 792-802.

International Searching Authority, International Search Report and Written Opinion, mailed Nov. 25, 2009 (PCT/US09/057800).

* cited by examiner

DEVICES, SYSTEMS, AND METHODS TO DETERMINE FRACTIONAL FLOW RESERVE

PRIORITY

The present application is related to, claims the priority benefit of, and is a U.S. continuation patent application of, U.S. patent application Ser. No. 13/120,308, filed Mar. 22, 2011 and issued as U.S. Pat. No. 8,702,613 on Apr. 22, 2014, which is related to, claims the priority benefit of, and is a U.S. national stage application of, International Patent Application Serial No. PCT/US2009/057800, filed Sep. 22, 2009, which is related to, and claims the priority benefit of, U.S. Provisional Patent Application Ser. No. 61/098,837, filed Sep. 22, 2008. The contents of each of these applications and patent are hereby incorporated by reference in their entirety into this disclosure.

BACKGROUND

Coronary heart disease remains the leading cause of morbidity and mortality in the United States and the developed world. Although the current "gold standard" for assessing coronary artery disease (CAD) is angiography, it has serious limitations in evaluating the functional significance of intermediate coronary lesions (comprising 30-70% stenosis). Coronary angiography relies on a visual interpretation of coronary anatomy. A number of studies have documented the large intra- and inter-observer variability that results from visual grading of coronary stenotic lesions. Moreover, studies have shown a lack of correlation between the angiographic delineated stenosis with their physiologic severity on coronary flow. This stems from the highly non-linear relation between the degree of stenosis and the change in blood flow. Typically, the blood flow remains unchanged until the degree of stenosis reaches a critical range (typically >80%), at which point the decrease in flow is quite dramatic. Lesions that are not functionally significant (i.e., do not reduce the flow) may not need treatment. Hence, there is a need for complementary methods to conventional coronary arteriograms that combine coronary anatomy and physiology to assess CAD accurately.

Blood vessel diameter or cross-sectional area gives anatomic measures of stenosis severity. Coronary blood flow, on the other hand, reflects coronary hemodynamic function and can be used to assess functional severity of stenosis through parameters such as coronary flow reserve (CFR) and fractional flow reserve (FFR). CFR, defined as the ratio of hyperemic (induced by pharmacological agents) to resting flow in a coronary artery. It has been previously found that a significant stenosis leading to inducible ischemia occurs when CFR has a value less than 2.0. Normally, the coronary circulation has a flow reserve of 3-5 times that of normal resting blood flow. This reserve stems from the tone of small blood vessels (microvascular bed). In disease, the microvascular bed dilates and uses some of its reserve to compensate for the pressure drop to the stenosis. Hence, a low CFR value can characterize disease in the epicardial arteries or the distal resistive microvascular bed.

CFR can be estimated from hyperemic and resting blood velocities measured by a Doppler guidewire. This method is based on the principle of Doppler which requires that the piezo-electric crystal to be at a specific angle to the flowing blood. Since this condition is very difficult to meet in clinical practice as the tip of the wire is difficult to align with the direction of flow, the measurements are not reliably accurate and this method has not enjoyed clinical utility. Recent developments have introduced methods and systems for accurate determination of cross-sectional area of blood vessels including coronary arteries. Simultaneous measurements of cross-sectional area and flow (including CFR) would provide a clinician with a greater insight in the contribution of the epicardial vessel and microvasculature to total resistance to myocardial blood flow.

In summary, there are well-known limitations to the use of visual estimation to assess the severity of coronary artery disease and luminal stenosis. This is especially true in the case of intermediate coronary lesion where coronary angiography is very limited in distinguishing ischemia-producing intermediate coronary lesions from non-ischemia-producing ones. For this reason, a functional measure of stenosis severity is desirable. Previous devices involving Doppler flow wires also have serious limitations as referenced above. Hence, there is clearly a need for a simple, accurate, cost effective solution to determination of coronary blood flow in routine practice.

BRIEF SUMMARY

In at least one embodiment of a method for determining fractional flow reserve within a luminal organ of the present disclosure, the method comprises the steps of positioning a device comprising at least two sensors within a luminal organ at or near a stenosis, wherein the at least two sensors are separated a predetermined distance from one another, operating the device to determine flow velocity of a second fluid introduced into the luminal organ to temporarily displace a first fluid present within the luminal organ, and determining fractional flow reserve at or near the stenosis based upon the flow velocity, a mean aortic pressure within the luminal organ, and at least one cross-sectional area at or near the stenosis. In at least one embodiment, the at least one cross-sectional area comprises a cross-sectional area of the luminal organ distal to the stenosis, a cross-sectional area of the luminal organ proximal to the stenosis, and at least one cross-sectional area of the luminal organ at the stenosis.

In another exemplary embodiment of a method for determining fractional flow reserve within a luminal organ of the present disclosure, the step of determining fractional flow reserve is further based upon a determination of volumetric flow between the at least two sensors. In an additional embodiment, the determination of volumetric flow is based upon the flow velocity and the at least one cross-sectional area.

In an exemplary embodiment of a method for determining fractional flow reserve within a luminal organ of the present disclosure, the step of operating the device to determine flow velocity of a fluid introduced into the luminal organ comprises the steps of detecting the first fluid within the luminal organ using at least one of the at least two sensors, wherein the first fluid has a first parameter having a first value, introducing the second fluid into the luminal organ, said second fluid temporarily displacing the first fluid within the luminal organ at the site of introduction, wherein the second fluid has a second parameter having a second value, the second value differing from the first value, detecting the second value of the second parameter of the second fluid by the at least two sensors, measuring time of detection of the second value of the second parameter of the second fluid by each of the at least two sensors, and determining flow velocity of the second fluid within the luminal organ based upon the time of detection of the second value of the second parameter of the second fluid by each of the at least two sensors. In at least one embodiment, the first parameter and the second parameter are conductivity, pH, temperature, or an optically-detectable substance. In another exemplary embodiment, the method further comprises the step of diagnosing a disease based upon the determination of flow velocity within a luminal organ. In yet another embodiment, the determination of fractional flow reserve is indicative of a degree of stenosis within the lumina organ. In an exemplary embodiment, the step of determining fractional flow reserve is performed using a data acquisition and processing system. In at least one embodiment, the first fluid comprises blood and the second fluid comprises saline.

In at least one embodiment of a method for determining fractional flow reserve within a luminal organ of the present disclosure, the method is bawd upon at least the detection of an introduced bolus within a luminal organ, wherein the introduced bolus has a parameter with a value different from the value of the parameter of the fluid present within the luminal organ prior to the introduction of the bolus.

In at least one embodiment of a method for determining fractional flow reserve within a luminal organ using impedance of the present disclosure, the method comprises the steps of positioning a device comprising a pair of excitation electrodes and at least two pairs of detection electrodes within a luminal organ at or near a stenosis, wherein the at least two pairs of detection electrodes are separated a predetermined distance from each other, operating the device to determine flow velocity of a second fluid introduced into the luminal organ, said second fluid temporarily displacing a first fluid present within the luminal organ, and determining fractional flow reserve at or near the stenosis based upon the flow velocity, a mean aortic pressure within the luminal organ, and at least one cross-sectional area at or near the stenosis. In at least one embodiment, the at least one cross-sectional area comprises a cross-sectional area of the luminal organ distal to the stenosis, a cross-sectional area of the luminal organ proximal to the stenosis, and at least one cross-sectional area of the luminal organ at the stenosis.

In at least one embodiment of a method for determining fractional flow reserve within a luminal organ using impedance of the present disclosure, the step of determining fractional flow reserve is further based upon a determination of volumetric flow between the at least two pairs of detection electrodes. In another embodiment, the determination of volumetric flow is based upon the flow velocity and the at least one cross-sectional area.

In at least one embodiment of a method for determining fractional flow reserve within a luminal organ using impedance of the present disclosure, the step of operating the device to determine flow velocity of a fluid introduced into the luminal organ comprises the steps of activating the pair of excitation electrodes to generate a field detectable by the detection electrodes, detecting conductance of the first fluid having a first conductivity within the luminal organ using at least one pair of the at least two pairs of detection electrodes, introducing the second fluid having a second conductivity into the luminal organ, said second fluid temporarily displacing the first fluid within the luminal organ at the site of introduction, wherein the first conductivity does not equal the second conductivity, detecting the conductance of the second fluid by the at least two pairs of detection electrodes, measuring time of conductance detection of the second fluid by each of the at least two pairs of detection electrodes, and determining flow velocity of the second fluid within the luminal organ based upon the time of conductance detection by each of the at least two pairs of detection electrodes.

In at least one embodiment of a method for determining fractional flow reserve within a luminal organ using impedance of the present disclosure, the step of operating the device to determine flow velocity of a fluid introduced into the luminal organ comprises the steps of activating the pair of excitation electrodes to generate a field, detecting conductance of the first fluid having a first conductivity within the luminal organ using at least one pair of the at least two pairs of detection electrodes, introducing the second fluid having a second conductivity into the luminal organ, said second fluid temporarily displacing the first fluid within the luminal organ at the site of introduction, wherein the first conductivity does not equal the second conductivity, detecting the conductance of the second fluid by the at least two pairs of detection electrodes, measuring time of conductance detection of the second fluid using at least one pair of the at least two pairs of detection electrodes, and determining flow velocity of the second fluid within the luminal organ based upon the time of conductance detection using (a) a first excitation electrode of the pair of excitation electrodes and a first pair of detection electrodes of the at least two pairs of detection electrodes, and (b) a second excitation electrode of the pair of excitation electrodes and a second pair of detection electrodes of the at least two pairs of detection electrodes.

In at least one embodiment of a method for determining fractional flow reserve within a luminal organ using impedance of the present disclosure, the method further comprises the step of diagnosing a disease based upon the determination of flow velocity within a luminal organ. In another embodiment, the determination of fractional flow reserve is indicative of a degree of stenosis within the luminal organ. In yet another embodiment, the step of determining fractional flow reserve is performed using a data acquisition and processing system. In at least one exemplary embodiment, the first fluid comprises blood and the second fluid comprises saline.

In at least one embodiment of a method for determining fractional flow reserve within a luminal organ using impedance of the present disclosure, the method is based upon at least the detection of an introduced bolus within a luminal organ, wherein the introduced bolus has a conductivity different from the conductivity of the fluid present within the luminal organ prior to the introduction of the bolus.

In at least one embodiment of a device for determining fractional flow reserve of a fluid within a luminal organ of the present disclosure, the device comprises an elongated body sized and shaped to fit within a luminal organ, and at least two sensors positioned along the elongated body a predetermined distance from one another, wherein the device is operable to detect a first fluid with a first parameter having a first value using at least one of the at least two sensors when the device is positioned within the luminal organ, and wherein the device is further operable to detect a second fluid having a second parameter, wherein the second parameter of the second fluid has a second value different from the first value, upon introduction of the second fluid within the luminal organ at or near the at least two sensors. In at least one embodiment, the second fluid detected by the at least two sensors allows for the determination of flow velocity based upon timing of the detected second fluid by the at least two sensors and the distance between the at least two sensors. In another embodiment, the device is further operable to determine fractional flow reserve when the device is positioned within the luminal organ at or near a stenosis, wherein the fractional flow reserve is based upon the flow velocity, a mean aortic pressure within the luminal organ, and at least one cross-sectional area at or near the stenosis. In yet another embodiment, the at least one cross-sectional area comprises a cross-sectional area of the luminal organ distal to the stenosis, a cross-sectional area of the luminal organ proximal to the stenosis, and at least one cross-sectional area of the luminal organ at the stenosis.

In at least one embodiment of a device for determining fractional flow reserve of a fluid within a luminal organ of the present disclosure, the flow velocity allows for the determination of volumetric flow based upon the flow velocity and a cross-sectional area of the luminal organ. In another embodiment, the determination of fractional flow reserve is made using a data acquisition and processing system.

In at least one embodiment of a device for determining fractional flow reserve of a fluid within a luminal organ of the present disclosure, the device comprises an elongated body sized and shaped to fit within a luminal organ, at least one pair of excitation electrodes positioned along the elongated body, and at least two pairs of detection electrodes positioned along the elongated body between the at least one pair of excitation electrodes, wherein the at least two pairs of detection electrodes are positioned a predetermined distance from each other, wherein when the device is positioned within the luminal organ, the device is operable to detect a first conductance of a first fluid having a first conductivity within the luminal organ using the at least two pairs of detection electrodes, the device further operable to detect a second conductance of a second fluid having a second conductivity using the at least two pairs of detection electrodes upon introduction of the second fluid within the luminal organ at or near the at least two pairs of detection electrodes. In at least one embodiment, the second fluid detected by using the at least two pairs of detection electrodes allows for the determination of flow velocity based upon timing of the detected second fluid by using the at least two pairs of detection electrodes and the distance between the at least two pairs of detection electrodes.

In at least one embodiment of a system for determining fractional flow reserve of a fluid within a luminal organ of the present disclosure, the system comprises a device for determining fractional flow reserve, the device comprising an elongated body sized and shaped to fit within a luminal organ, and at least two sensors positioned along the elongated body a predetermined distance from one another, wherein the device is operable to detect a first fluid with a first parameter having a first value using at least one of the at least two sensors when the device is positioned within the luminal organ, and wherein the device is further operable to detect a second fluid having a second parameter, wherein the second parameter of the second fluid has a second value different from the first value, upon introduction of the second fluid within the luminal organ at or near the at least two sensors, and a data acquisition and processing system in communication with the device, the data acquisition and processing system operable to calculate flow velocity of the second fluid based upon timing of the detected second fluid by the at least two sensors and the distance between the at least two sensors.

In at least one embodiment of a system for determining fractional flow reserve of a fluid within a luminal organ of the present disclosure, the system comprises a device for determining fractional flow reserve, the device comprising an elongated body sized and shaped to fit within a luminal organ, at least one pair of excitation electrodes positioned along the elongated body, and at least two pairs of detection electrodes positioned along the elongated body between the at least one pair of excitation electrodes, wherein the at least two pairs of detection electrodes are positioned a predetermined distance from each other, wherein when the device is positioned within the luminal organ, the device is operable to detect a first conductance of a first fluid having a first conductivity within the luminal organ using the at least two pairs of detection electrodes, the device further operable to detect a second conductance of a second fluid having a second conductivity using the at least two pairs of detection electrodes upon introduction of the second fluid within the luminal organ at or near the at least two pairs of detection electrodes, and a data acquisition and processing system in communication with the device, the data acquisition and processing system operable to calculate flow velocity of the second fluid based upon timing of the detected second fluid by using the at least two pairs of detection electrodes and the distance between the at least two pairs of detection electrodes.

In at least one embodiment of a system for determining fractional flow reserve of a fluid within a luminal organ of the present disclosure, the data acquisition and processing system is further operable to determine fractional flow reserve when the device is positioned within the luminal organ at or near a stenosis, wherein the fractional flow reserve is based upon the flow velocity, a mean aortic pressure within the luminal organ, and at least one cross-sectional area at or near the stenosis. In another embodiment, the flow velocity allows for the determination of volumetric flow based upon the flow velocity and a cross-sectional area of the luminal organ.

DETAILED DESCRIPTION

Figure 1:
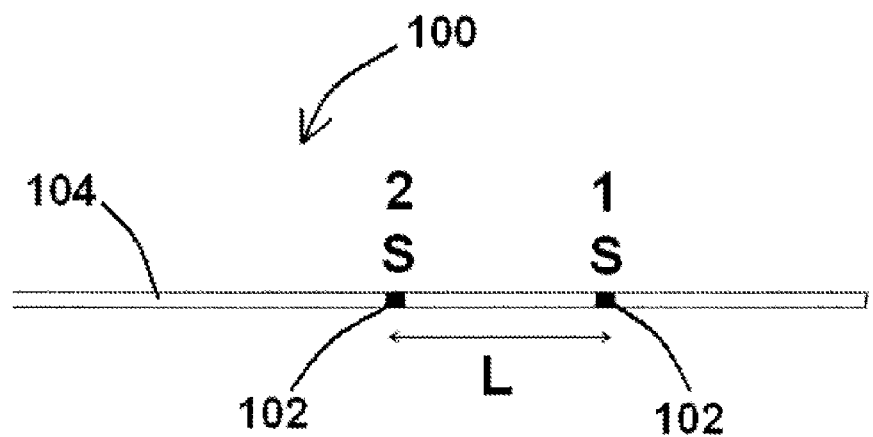
FIG. 1 shows an exemplary embodiment of a portion of a device useful for determining flow velocity and volumetric flow comprising two sensors positioned along a body of the device, according to the disclosure of the present application.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The disclosure of the present application provides devices, systems, and methods for determining fractional flow reserve (FFR), including devices, systems, and methods for determining FFR using impedance. An exemplary method for performing the same would utilize one or more devices (or elements/features of such a device) operable to detect a change in at least one characteristic within a vessel flow based upon the introduction of a change to the initial flow. Such methods, and devices and systems for performing such methods, are useful for the diagnosis of disease (including CAD) by providing accurate values for flow velocity, whereby changes in flow velocity and/or volumetric flow may be indicative of a low or high degree of stenosis. Such changes in flow velocity and/or volumetric flow may be identified by comparing flow velocity and/or volumetric flow at various vessels and/or organs (generally referred to as "luminal organs") within a body, and or by comparing flow velocity and/or volumetric flow taken at various times.

For purposes of the present application, an "indicator" shall mean a substance introduced to, for example, a blood vessel, that includes at least one parameter different than the native fluid flowing within such a vessel, which may include, but is not limited to, various chemical changes like osmolarity and pH, for example, and/or optical, electrical, and/or thermal changes. Exemplary indicators may then be detectable by a "sensor," which may comprise any number of applicable sensors useful to detect such indicators. Exemplary sensors may include, but are not limited to, detection electrodes, pH sensors, thermocouples, and optical sensors, which are operable to detect one or more indicators. A "parameter," as referenced herein, refers to an aspect of an indicator that may be detected by one or more sensors, including, but not limited to, conductivity, pH, temperature, and/or optically-detectable substances. The disclosure of the present application is not intended to be limited to the specific indicators and/or sensors disclosed herein, as other indicators and/or sensors suitable for the devices, systems, and methods for determining FFR not disclosed herein may also be suitable for one or more applications of the same.

An exemplary embodiment of at least a portion of a device useful for determining FFR using impedance is shown in FIG. 1. As shown in FIG. 1, device 100 comprises two sensors 102 (each sensor 102 labeled "S" in FIG. 1, whereby one sensor 102 is further labeled "1" and the second sensor 102 is further labeled "2") positioned along the body 104 of device 100 at or near the distal end of device 100. Various embodiments of device 100 as described herein may comprise two or more sensors 102, and sensors 102 may be positioned along various portions of body 104 of device 100. Additionally, device 100 may comprise any number of suitable devices 100 with the characteristics/components described herein, which may include, but are not limited to, catheters and guidewires. For example, device 100 may comprise a standard catheter, a balloon catheter, an angioplasty catheter, a fluid-filled silastic pressure-monitoring catheter, a standard wire, an impedance wire, a guidewire, and other catheters or wires that may include the characteristics of a device 100 as described herein.

In the embodiment shown in FIG. 1, sensors 102 are separated by a distance L as shown therein. As discussed in greater detail herein, an exemplary method for determining FFR is based upon the principle that two or more sensors 102 spaced at a predetermined distance apart can "time" the injection of a bolus injection as the plug flow moves past the sensors 102 sequentially (e.g., sensor 102 "1" first, and then sensor 102 "2" as shown in FIG. 1). Upon detection of the bolus by sensors 102 in accordance with the present application, a determination of flow velocity may be determined based upon the distance between the two sensors 102 (L) and the time difference between the detection of the bolus by sensors 102. As previously referenced herein, such a bolus may include and/or comprise one or more indicators (e.g., a hyper-osmotic solution, a hypo-osmotic solution, a solution of a pH different from the native fluid flowing within the target vessel, a solution of a different temperature than the native fluid flowing within the target vessel, etc.) detectable by sensors 102 (e.g., detection electrodes, pH sensors, thermocouples, etc.) positioned along the body 104 of device 100, so that the indicator(s), when introduced to a vessel containing device 100, are detectable at various times by the sensor(s) 102 positioned along device 100.

Figure 6:
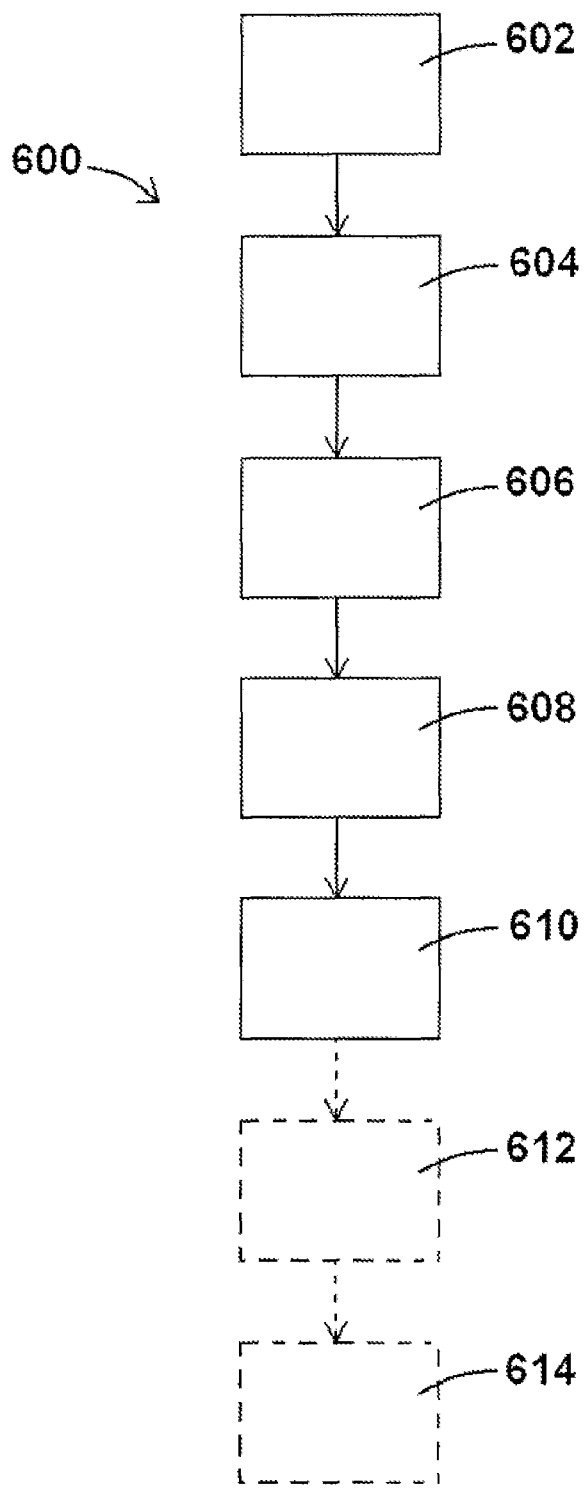
FIG. 6 shows a block diagram of a method for determining flow velocity according to the disclosure of the present application.

In at least one embodiment of a method for determining FFR, a device 100 comprising two or more sensors 102 is useful for performing said method. An exemplary method of the disclosure of the present application comprises the steps of inserting such a device 100 into a vessel with a fluid flow and injecting/introducing a bolus (either from said device 100 or another device) which can be detected by sensors 102. In at least one embodiment of a method 600 for determining FFR of the present disclosure, and as shown in the block diagram of FIG. 6, method 600 comprises the step of positioning a device 100 comprising at least two sensors 102 within a vessel or organ (positioning step 602), wherein the at least two sensors 102 are separated a known distance from one another. Such a method 604 further comprises the steps of detecting at least one parameter of a first fluid within the vessel or organ using sensors 102 (first detection step 604), and injecting a second fluid having at least one parameter different than the at least one parameter of the first fluid into the vessel or organ to temporarily displace the first fluid at the site of injection (injection step 606). An exemplary method 600 of the present disclosure further comprises the steps of detecting at least the different parameter of the second fluid by sensors 102 (second detection step 608) and measuring the time of detection of the second fluid by each of the at least two sensors 102 (measuring step 610). An exemplary method 600 may further comprise the step of determining flow velocity of the second fluid within the vessel or organ based upon the time of detection of the second fluid by each of the at least two sensors 102 (flow velocity determination step 612). An additional exemplary method 600 of the present disclosure may further comprise the step of determining FFR based upon volumetric flow and a cross-sectional area of the vessel or organ (FFR determination step 614) as described in further detail herein.

Figure 2:
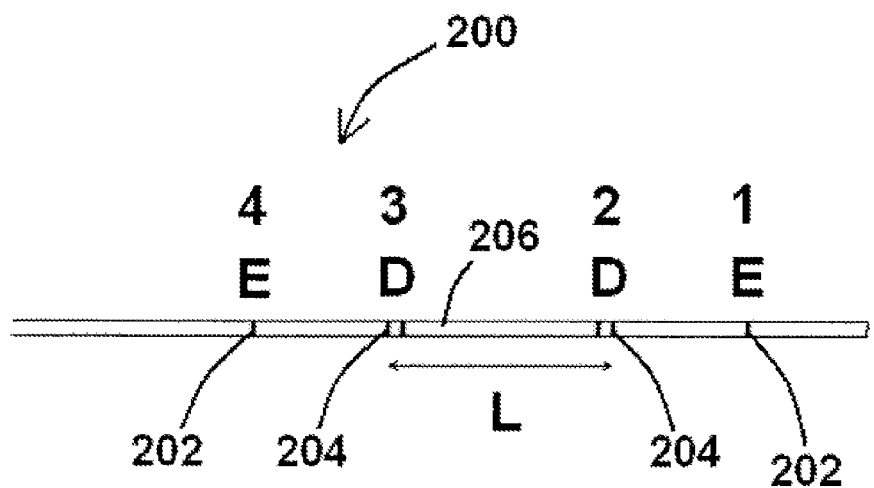
FIG. 2 shows an exemplary embodiment of a portion of a device useful for determining flow velocity and volumetric flow comprising a hexa-polar (six electrode) arrangement of electrodes with two outer electrodes (E) and two sets of detection electrodes (D), according to the disclosure of the present application.

An exemplary embodiment of at least a portion of a device useful for determining FFR using impedance is shown in FIG. 2. As shown the exemplary embodiment in FIG. 2, device 200 comprises at least one pair of excitation electrodes 202 (each excitation electrode 202 labeled "E" in FIG. 2) and at least two pairs of detection electrodes 204 (each pair of detection electrodes 204 labeled "D" in FIG. 2) positioned along the body 206 of device 200 at or near the distal end of device 200. Such an arrangement of three pairs of electrodes (one pair of excitation electrodes 202 and two pairs of detection electrodes 204) is referred to herein as a "hexa-polar" arrangement. Excitation electrodes 202, when activated, provide an electric field (not shown) between the excitation electrodes 202 so that detection electrodes 204, when activated, may detect the electric field.

Additional devices other than at least the portion of device 200 shown in FIG. 2 are also considered to be within the scope of the present application. For example, an exemplary device 200 may comprise more electrodes than the hexa-polar arrangement of electrodes shown in FIG. 2. For example, additional exemplary devices 200 may contain one pair of excitation electrodes 202 and three pairs of detection electrodes 204, and may further include devices 200 containing two pairs of detection electrodes 202 spaced a distance apart from one another so not to interfere with the excitation field of each pair of detection electrodes 202, whereby each of the two pairs of excitation electrodes 202 has at least one pair of detection electrodes 204 positioned therebetween. In at least one exemplary embodiment of a device 200 of the present disclosure, device 200 comprises one pair of excitation electrodes 202 and five pairs of detection electrodes 204 spaced known distance(s) apart from one another.

As referenced above, detection electrodes 204 operate to detect a electric field generated by a pair of excitation electrodes 202, and therefore, at least one pair of detection electrodes 204 must be positioned in between the pair of excitation electrodes 202 in order to properly detect the field as referenced herein. Accordingly, and for example, an additional embodiment of a device 200 comprising one pair of excitation electrodes 202 and three pairs of detection electrodes 204 positioned therebetween would allow for three separate field detections, namely one detection by each of the three pairs of detection electrodes 204.

An embodiment of a device 200 comprising two pairs of excitation electrodes 202 and a pair of detection electrodes 204 positioned between each pair of excitation electrodes 202 would allow each pair of detection electrodes 204 to each detect a field generated by each pair of excitation electrodes 202. The various embodiments referenced herein are merely exemplary embodiments of devices 200 of the disclosure of the present application, and other embodiments of devices 200 are hereby contemplated within the disclosure of the present application.

Additionally, device 200 may comprise any number of suitable devices 200 with the characteristics/components described herein, which may include, but are not limited to, catheters and guidewires. For example, device 200 may comprise a standard catheter, a balloon catheter, an angioplasty catheter, a fluid-filled silastic pressure-monitoring catheter, a standard wire, an impedance wire, a guidewire, and other catheters or wires that may include the characteristics of a device 200 as described herein.

Figure 5:
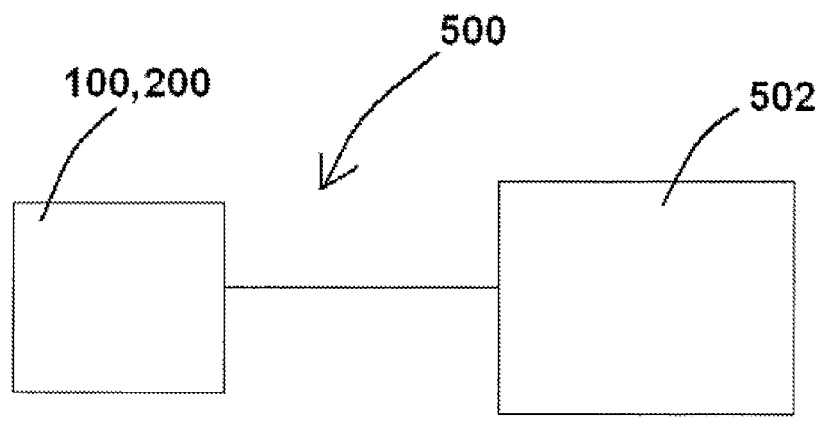
FIG. 5 shows an exemplary embodiment of a system useful for determining flow velocity and volumetric flow according to the disclosure of the present application.

Devices 100, 200 of the present disclosure may be part of a system 500 as shown in the exemplary block diagram embodiment of a system for determining FFR using impedance of the present disclosure shown in FIG. 5. As shown in FIG. 5, system 500 comprises device 100, 200 (or other devices in accordance with the present application) and a data acquisition and processing system 502 in communication with the device 100, 200, wherein the data acquisition and processing system 502 is operable to calculate flow velocity of a fluid based upon the detection of the fluid within a vessel or organ by the sensors 102 coupled to device 100 or the detection electrodes 204 coupled to device 200. An exemplary data acquisition and processing system 502 may comprise, for example, a computer or another electronic device capable of receiving data from sensors 102 or detection electrodes 204 and processing such data to determine flow velocity, volumetric flow, and/or FFR.

In at least one embodiment of a method for determining FFR using impedance, a device 200 comprising multiple excitation electrodes 202 and detection electrodes 204 is useful for performing said method. An exemplary method of the disclosure of the present application comprises the steps of inserting such a device 200 into a vessel with a fluid flow and injecting a bolus (either from said device 200 or another device) which can be detected by the detection electrodes 204.

Figure 7:
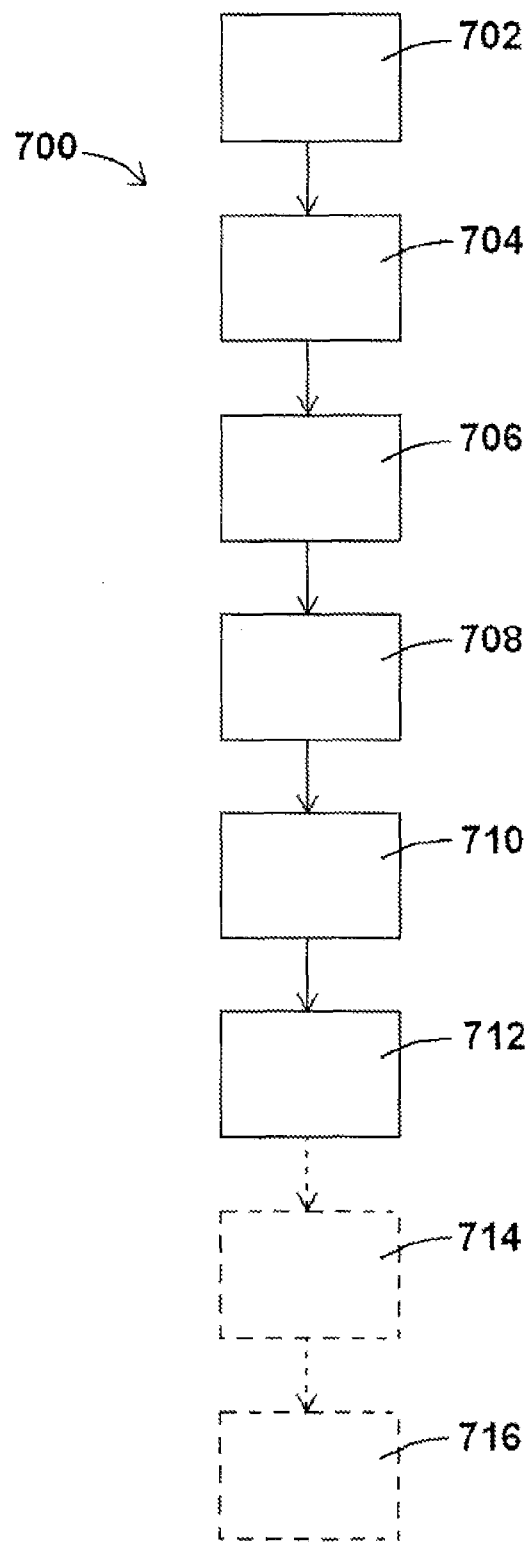
FIG. 7 shows a block diagram of a method for determining flow velocity using impedance according to the disclosure of the present application.

In at least one embodiment of a method 700 for determining FFR using impedance of the present disclosure, as shown in the block diagram of FIG. 7, method 700 comprises the steps of positioning a device 200 comprising excitation electrodes 202 and at least two pairs of detection electrodes 204 within a vessel or organ (positioning step 702), wherein the at least two pairs of detection electrodes 204 are separated a known distance from one another. The excitation electrodes 202 may then be activated to generate an electric field detectable by the detection electrodes 204 (field generation step 704). Such a method 700 further comprises the steps of detecting the conductance of a first fluid having a first conductivity within the vessel or organ using the detection electrodes 204 (first conductance detection step 706), and injecting a second fluid having a second conductivity into the vessel or organ to temporarily displace the first fluid at the site of injection (injection step 708). An exemplary method 700 of the present disclosure further comprises the steps of detecting the conductance of the second fluid by the at least two pairs of detection electrodes 204 (second conductance detection step 710) and measuring the time of conductance detection by each of the at least two pairs of detection electrodes 204 (measuring step 712). An exemplary method 700 may further comprise the step of determining flow velocity of the second fluid within the vessel or organ based upon the time of conductance detection by each of the at least two pairs of detection electrodes 204 (flow velocity detection step 714). An additional exemplary method 700 of the present disclosure may further comprise the step of determining FFR based upon volumetric flow and a cross-sectional area of the vessel or organ (FFR determination step 716) as described in further detail herein.

Such a method is based upon the principle that two sensors spaced at some distance apart (for example, the two pairs of detection electrodes 204 separated by a distance L as shown in FIG. 2), can time the injection of a bolus injection as the plug flow moves past the two sensors sequentially. Upon detection of the bolus by the two pairs of detection electrodes 204 in accordance with the present disclosure, a determination of flow velocity may be determined based upon the distance between the two detection electrodes 204, L, and the time difference between the detection of the bolus by the two pairs of detection electrodes 204.

Figure 3A:
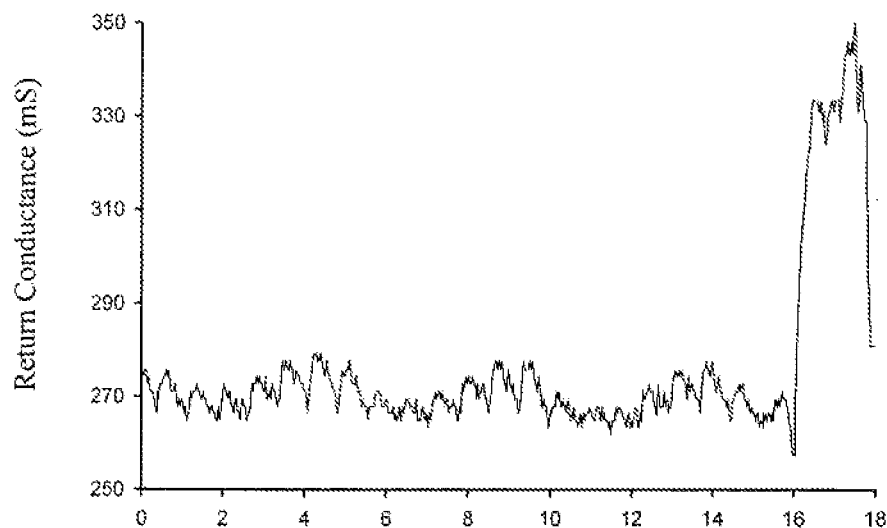
FIG. 3A shows a graph demonstrating the increase in total conductance over time during a transient injection of 1.5% sodium chloride solution into a pig coronary artery in accordance with at least one method of the disclosure of the present application.
Figure 3B:
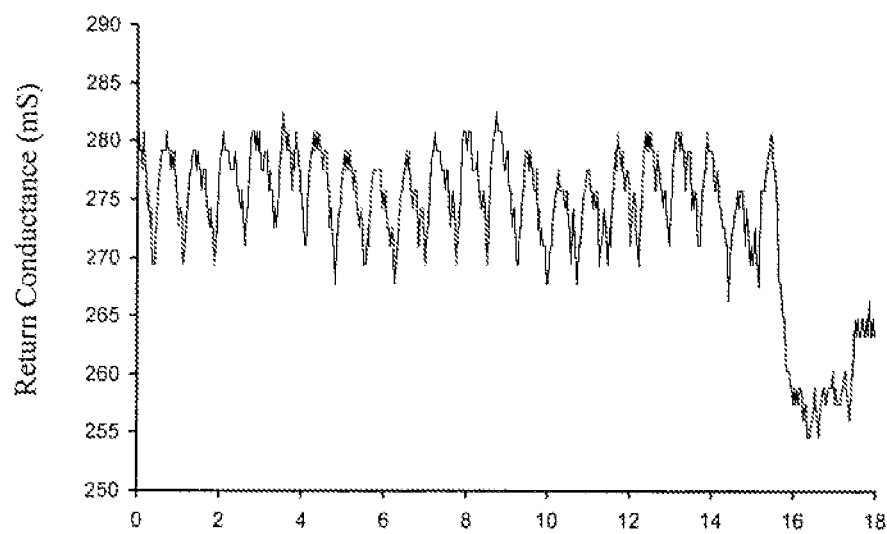
FIG. 3B shows a graph demonstrating the decrease in total conductance over time during a transient injection of 0.45% sodium chloride solution into a pig coronary artery in accordance with at least one method of the disclosure of the present application.
Figure 4:
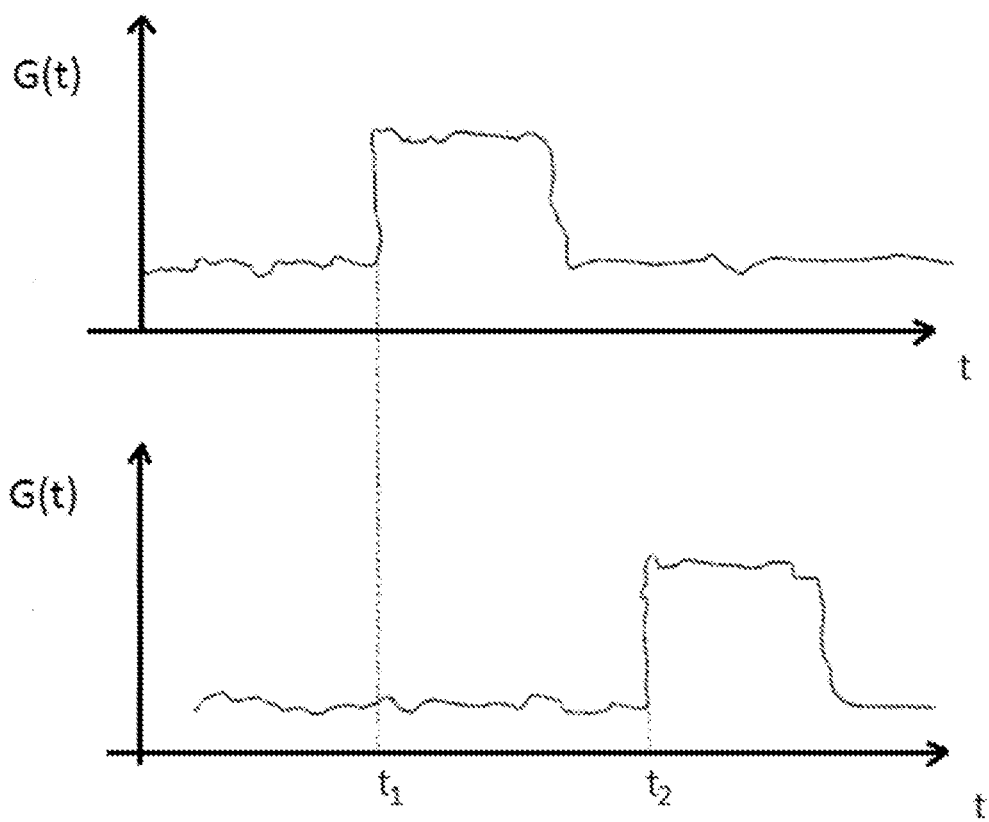
FIG. 4 shows changes in conductance over time at electrodes 1 and 2 (as shown in FIG. 2) during a 0.9% sodium chloride injection in accordance with at least one method of the disclosure of the present application.

The use of either hyper-osmotic or hypo-osmotic solution can be detected by detection electrodes 204 as shown in FIGS. 3A and 3B, respectively. If, in accordance with the disclosure of the present application, one combines this detection concept with a hexa-polar arrangement of electrodes (as shown in FIG. 2, for example) with a single injection of either a hyper-osmotic solution or a hypo-osmotic solution (or saline, for example, as shown in FIG. 3A), the sequential detection of the saline solution can be made by the two sets of detection electrodes 204 (labeled as "1" and "2" in FIG. 2). Accordingly, the time (t) interval between the passing bolus can be determined as the difference between the times detected at the two separate positions:

$$\Delta t = t_2 - t_1 \quad [1]$$

Hence, the velocity, V, of the bolus is given by the following formula:

$$V = L/\Delta t \quad [2]$$

wherein L is the length between the sensors, and the volumetric flow is as follows:

$$Q = V * CSA \quad [3]$$

where cross-sectional area, CSA, may be determined using any number of suitable methods and/or devices for performing the same.

The equation governing the physics of electrical conductance in a blood vessel is given by:

$$G(t) = \frac{CSA(t) \cdot \sigma}{L} + G_p(t) \quad [4]$$

wherein G (the conductance) is the ratio of the current induced by the excitation electrodes 202 and the potential difference between the detection electrodes 204, CSA is the cross-sectional area of a vessel, σ is the specific conductivity of the fluid, L is the distance between detection electrodes 204, $G_p$ is an offset error resulting from current leakage and is the effective parallel conductance of the structure outside the vessel lumen (vessel wall and surrounding tissue), and t is the time in the cardiac cycle.

If the following is considered:

$$G_p = \gamma \frac{CSA \cdot \sigma}{L} \quad [5]$$

wherein γ is a constant, Equation [4] can be expressed as $$G = \frac{I}{\Delta V} = \frac{CSA \cdot \sigma}{L}(1 + \gamma) \quad [6]$$

wherein I is the current through electrodes 1 and 4 (as shown in FIG. 2, for example), and ΔV is the voltage drop. The electric resistance in a blood vessel, R, is given by:

$$R = \frac{1}{G} = \frac{\Delta V}{I} = \frac{L}{CSA \cdot \sigma \cdot (1 + \gamma)} \quad [7]$$

In such an embodiment, and as referenced above, excitation electrodes 202 (electrodes numbered "1" and "4" in FIG. 2) create the field and also serve to simultaneously detect the various fluid parameters as referenced herein.

In order to calculate the flow rate/velocity using devices 100, 200 of the present disclosure, a solution (such as saline, for example) is infused into the vessel lumen over sensor 100 positioned along device 100 or detection electrodes 204 positioned along device 200 as previously referenced therein. Pairs of excitation electrodes 202, in at least one embodiment, are used as detectors since they are spaced further apart relative to detection electrodes 204, therefore providing a more accurate time of passage.

Figure 8:
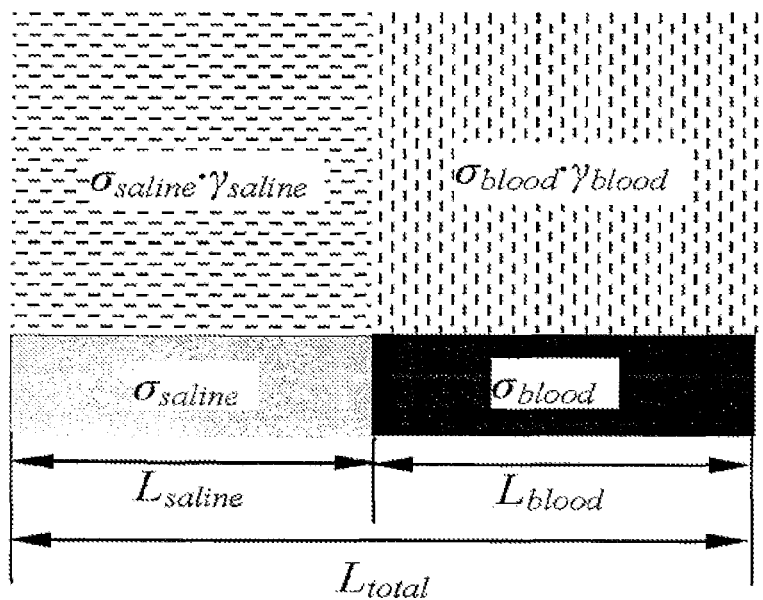
FIG. 8 shows a schematic of displacement of saline by blood after the injection of saline according to the disclosure of the present application.

FIG. 8 shows a schematic of displacement of saline by blood after the injection of saline. As shown in FIG. 8, the grey and black plots represent the saline solution and blood in the vessel lumen, respectively, and the dashed horizontal and vertical plots represent the vessel wall and tissues surrounding the vessel segments with saline solution and blood, respectively. Equation [7] can therefore be written as follows:

$$\frac{\Delta V_{total}}{I} = \frac{\Delta V_{blood}}{I} + \frac{\Delta V_{saline}}{I} \quad [8]$$

$$= \frac{L_{blood}}{CSA \cdot \sigma_{blood} \cdot (1 + \gamma_{blood})} + \frac{L_{saline}}{CSA \cdot \sigma_{saline} \cdot (1 + \gamma_{saline})}$$

$$= \frac{L}{CSA \cdot \sigma_{blood} \cdot (1 + \gamma_{blood})} + L_{saline}\left(\frac{1}{CSA \cdot \sigma_{saline} \cdot (1 + \gamma_{saline})} - \frac{1}{CSA \cdot \sigma_{blood} \cdot (1 + \gamma_{blood})}\right)$$

wherein $\Delta V_{total}$ is the total voltage difference of both saline and blood interface spanning the electrodes (FIG. 8), $V_{blood}$ is the voltage difference of blood (right side of FIG. 8), $\Delta V_{saline}$ is the voltage difference across saline portion (left side of FIG. 8), $L_{blood}$ is the blood segment length, $L_{saline}$ is the saline segment length, $\sigma_{blood}$ is the specific conductivity of blood, $\sigma_{saline}$ is the specific conductivity of saline, $\gamma_{blood}$ is a blood constant, and $\gamma_{saline}$ is a saline constant. If a constant α is defined as $$\alpha = \frac{1}{CSA \cdot \sigma_{saline} \cdot (1 + \gamma_{saline})} - \frac{1}{CSA \cdot \sigma_{blood} \cdot (1 + \gamma_{blood})} \quad [9]$$

then Equation [8] can be written as:

$$\frac{\Delta V_{total}}{I} = \frac{\Delta V_{blood\,only}}{I} + \alpha L_{saline} \quad [10]$$

wherein $\Delta V_{blood\,only}$ is the voltage drop across the blood portion. If a constant flow rate of saline solution is assumed to flow (transport) through the vessel lumen, then $$L_{saline} = v \cdot \Delta t \quad [11]$$

wherein v is the mean flow velocity and Δt is the time. Equations [9] and [10] can be combined to give:

$$\Delta t = \frac{\Delta V_{total}}{I \cdot \alpha \cdot v} - \frac{\Delta V_{blood\,only}}{I \cdot \alpha \cdot v} \quad [12]$$

wherein I, α, and v are constant. Hence, a linear relationship exists between the change in time, Δt, and the voltage difference, $\Delta V_{total}$. Prior to the injection of saline solution into the vessel segment between detection electrodes 204, $L_{saline} = 0$, $\Delta t = 0$, and $\Delta V = \Delta V_{blood\,only}$. When the saline solution occupies the vessel segment between detection electrodes 204, $L_{saline} = L$, $\Delta t = \Delta t_{transport}$, and $\Delta V = \Delta V_{saline\,only}$.

Figure 9:
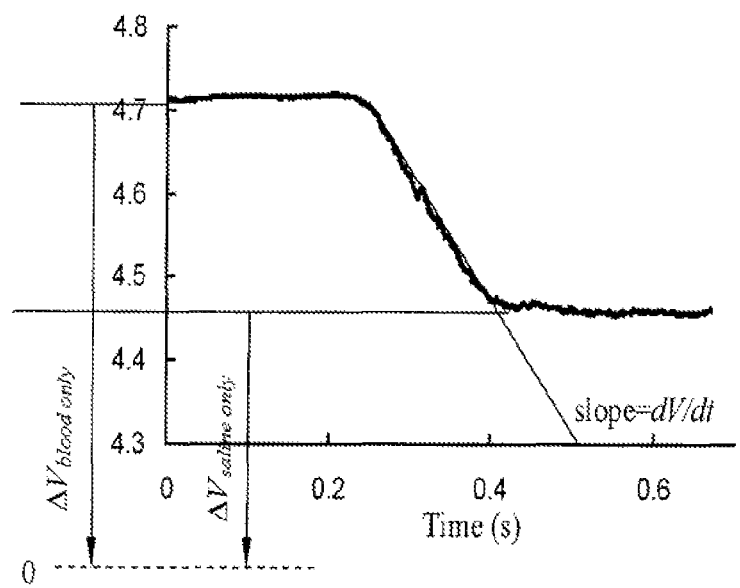
FIG. 9 shows a graph depicting the voltage drop across detection electrodes according to the disclosure of the present application.

The slope dV/dt, determined using an exemplary device 200 of the present application, is shown in FIG. 9 for a typical measurement made in a swine coronary artery. FIG. 9 shows a graph depicting the electric voltage drop across detection electrodes 204 as saline solution, for example, displaces blood present within a vessel. A decrease in voltage, as shown in FIG. 9, implies an increase in conductance.

As shown in FIG. 9, $\Delta V_{blood\,only}$ and $\Delta V_{saline\,only}$ are measured using an exemplary device 200 such that $$\Delta t_{transport} = |\Delta V_{saline}^{full} - \Delta V_{blood}^{full}|/(dV/dt) \quad [13]$$

wherein $\Delta_{transport}$ is the desired $\Delta t$, $\Delta V_{full\,saline}$ is the voltage drop if only saline is present (i.e., when blood is fully displaced), and $\Delta V_{full\,blood}$ is the voltage drop if only blood is present (i.e., when blood washes out saline). After the velocity is determined, the flow rate in the vessel segment can be calculated according to the conservation of mass, namely $$Q = \overline{CSA} \cdot v = \overline{CSA} \cdot L / \Delta t_{transport} \quad [14]$$

wherein Q is the volumetric flow rate, and wherein $\overline{CSA}$ is the mean CSA of the profile given by the mean value theorem as:

$$Q = v \frac{\int \overline{CSA}\,dx}{\int dx} \quad [15]$$

The integrals are evaluated over the profile between the proximal and distal measurements.

Figure 10:
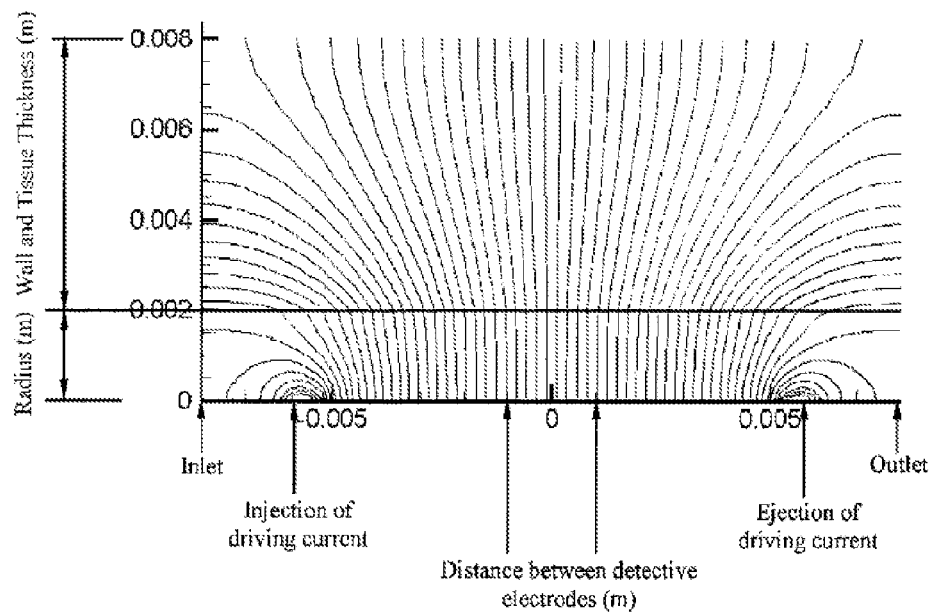
FIG. 10 shows a schematic of isopotential field lines for a coronary artery according to the disclosure of the present application.

As referenced herein, excitation electrodes 202 can measure the time of passage of the saline injection to provide the velocity since the spacing between the excitation electrodes 202 is known. The basic concept is that a junction potential is created when the blood displaces the injected saline, and this junction potential deflection is linear is shown below. FIG. 10 shows preliminary measurements of flow velocity in the swine coronary artery using a flowmeter (Transonic, Inc.) and an exemplary device 200 of the present disclosure in three animals, noting that the least-square fit shows a linear relationship with a slope of 1.02 (a $R^2$ of 0.955), which is highly significant. As the CSA can be determined as referenced herein, the product of CSA and velocity yields the desired volumetric flow rate.

A finite element model was developed to validate the linear relationship between time $\Delta t$ and voltage difference $\Delta V_{total}$. The equation of continuity (conservation of electric charge) governing the distribution of electric potential, V, is given by Poisson's equation as $$\nabla \cdot J = -\frac{\partial \rho}{\partial t} \quad [16]$$

where the current density, J, is related to the electric potential as $J = \sigma \nabla V$ and $\rho$, $\sigma$, and $\nabla$ are the electric volume charge density, electric conductivity, and del operator, respectively. Equation [16] indicates that the electric current density diverging from a small volume per unit volume equals to the time rate of decrease of charge per unit volume at every point. In the present control volume, $\partial \rho / \partial t = 0$ except for specific boundaries where the driving current, I, is injected and ejected into the control volume. Therefore, Equation [16] can be simplified as $$\nabla \cdot (\sigma \nabla V) = -I \quad [17]$$

Figure 11:
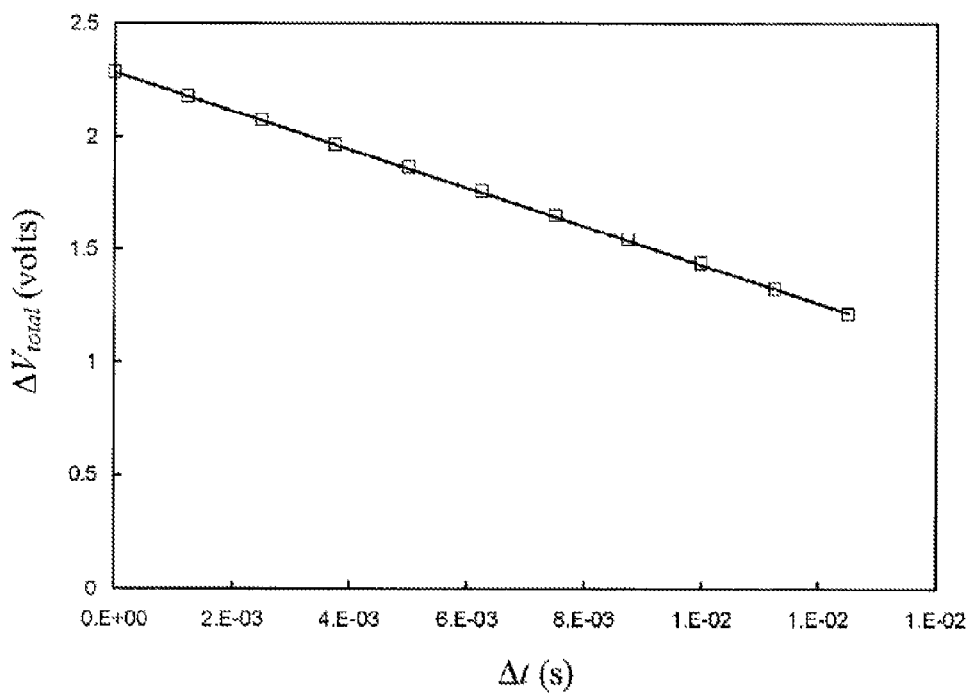
FIG. 11 shows a graph showing the validation of a finite element model according to the disclosure of the present application.

The Neumann boundary condition is applied to the external boundary except for the specific boundaries with the injection and ejection of driving current. A Galerkin finite element program was developed to calculate the nodal electric potential as shown in the isopotential contour plot of the electric field for a coronary artery with blood flows shown in FIG. 10. The isopotential field lines for a coronary artery shown in FIG. 10 simulate the deflection of voltage when saline solution is infused into the vessel lumen or when the saline is washed out by the blood, similar to the experimental measurements shown in FIG. 9. Finally, the relationship between time $\Delta t = L_2/v$ and voltage difference $\Delta V_{mix}$ was determined as represented by Equation [12]. The finite element model was then used to validate the linearity between $\Delta t$ and $\Delta V$ as shown in FIG. 11, which shows the relationship between $\Delta t$ and $\Delta V$ and a least-square fit of a perfect linear relationship ($R^2=1$).

Figure 12:
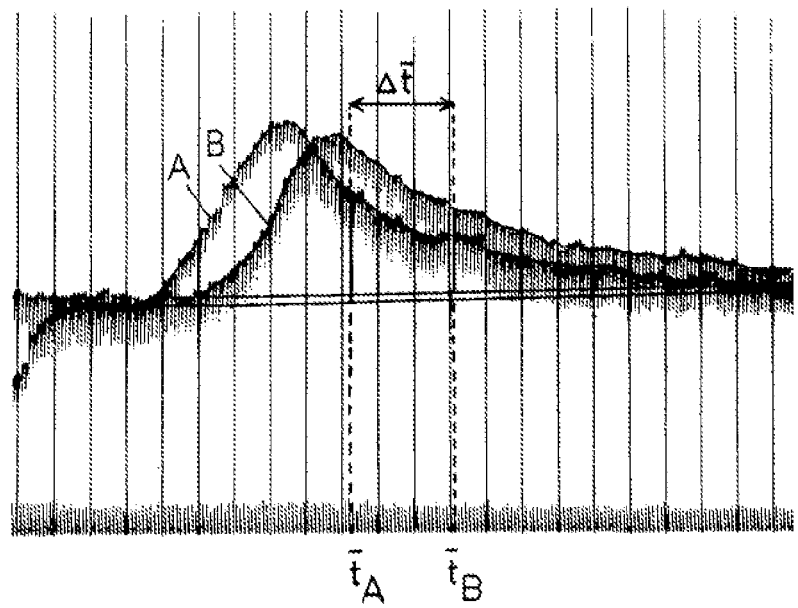
FIG. 12 shows a graph showing two sets of simultaneous voltage-time or conductance-time curves according to the disclosure of the present application.

The flow rate may also be determined as follows. If the electrodes of an exemplary device 200 of the present disclosure are referred to as 1, 2, 3 and 4 (as shown in FIG. 2), and as previously referenced herein, electrodes 1 and 4 represent excitation electrodes 202 and 2 and 3 represent detection electrodes 204 useful for the detection for measurement of diameter, for example. For velocity measurement, one can still excite at 1 and 4, but detection is simultaneously capable with 1 &2 and 3&4. This procedure provides two sets of simultaneous voltage-time (or conductance-time) curves as the bolus passes the electrodes as shown in FIG. 12. The shape of the curves is nearly identical but there is a time lag as shown in the figure.

The mean transit time for each curve can be calculated according to the mean value theorem, namely $$\bar{t} = \frac{\int tG(t)\,dt}{G(t)} \quad [18]$$

wherein G(t) is the measured electrical conductance and $\bar{t}$ is the mean transit time. The difference in mean transit time ($\Delta t$) can then be used to calculate the mean velocity since the distance between the electrodes travel by the fluid is known. When the velocity is determined as referenced herein, the flow rate in the vessel segment can be calculated according to conservation of mass as referenced in Equation [14]. The integrals are evaluated over the desired profile between the proximal and distal measurements.

The FFR is defined as:

$$FFR = \frac{P_{distal} - P_v}{P_a - P_v} \quad [19]$$

wherein $P_a$ is the mean aortic pressure, $P_v$ is the central venous pressure, and $P_{distal}$ is the hyperemic coronary pressure distal to stenosis. If venous pressure is assumed to be zero or remains unchanged, Equation [19] is further simplified to:

$$FFR = \frac{P_{distal}}{P_a} = \frac{P_a - \Delta P}{P_a} \quad [20]$$

wherein $\Delta P$ is the pressure gradient along the axis of vessel segment from proximal to distal portion of stenosis.

The determination of ΔP from a generated lumen profile based on conservation of momentum and energy is as follows. The Bernoulli equation (conservation of energy) is written as:

$$\Delta P = \frac{\rho Q^2}{2}\left(\frac{1}{CSA_{distal}^2} - \frac{1}{CSA_{proximal}^2}\right) + \sum \text{energy loss} \quad [21]$$

where $CSA_{proximal}$ and $CSA_{distal}$ are the proximal and distal cross-sectional areas of the lumen profile obtained by an exemplary device 200, respectively, and Q is the flow rate through the segment as obtained above. There are two major energy losses: diffusive energy loss and energy loss due to sudden enlargement in area from greatest stenosis (minimum CSA) to normal (distal) vessel segment.

Regarding diffusive energy loss, when the flow is assumed to be fully-developed in the vessel segment, the Poiseuille formula (conservation of momentum) is written as:

$$Q = -\frac{CSA^2}{8\pi\mu}\frac{dp}{dx} \quad [22]$$

wherein μ is the blood viscosity, and wherein dp/dx is the pressure gradient. Equation [22] may then be rewritten as:

$$-dp = \frac{8\pi\mu}{CSA^2}Q\,dx \quad [23]$$

wherein dx is the infinitesimal length of vessel. Integrating Equation [23] along the axis of vessel segment yields:

$$\Delta P_{viscous} = \int_0^{L_{total}} \frac{8\pi\mu}{CSA^2}Q\,dx \quad [24]$$

wherein $\Delta P_{viscous}$ is the pressure drop along the axis of vessel segment due to viscous diffusivity, and $L_{total}$ is the length of the distance between proximal and distal points of the profile as shown in FIG. 12.

The energy loss due to an abrupt expansion in area can be calculated approximately from the one-dimensional continuity, momentum and energy equations, which can be written as:

$$\Delta P_{expansion} = \frac{\rho Q^2}{2}\left(\frac{1}{CSA_{stenosis}} - \frac{1}{CSA_{distal}}\right)^2 \quad [25]$$

wherein ΔP expansion is the pressure drop due to an abrupt expansion in area, and wherein $CSA_{stenosis}$ and $CSA_{distal}$ are the cross-section areas at the stenosis and just distal to the stenosis, respectively. When Equations [24] and [26] are substituted into Equation [21], the following desired result is obtained:

$$\Delta P = \frac{\rho Q^2}{2}\left(\frac{1}{CSA_{distal}^2} - \frac{1}{CSA_{proximal}^2}\right) + \quad [26]$$

$$\int_0^{L_{total}} \frac{8\pi\mu}{CSA(x)^2}Q\,dx + \frac{\rho Q^2}{2}\left(\frac{1}{CSA_{stenosis}} - \frac{1}{CSA_{distal}}\right)^2$$

wherein $CSA_{distal}$ is the cross-sectional area at the distal end of the vessel lesion.

Figure 13:
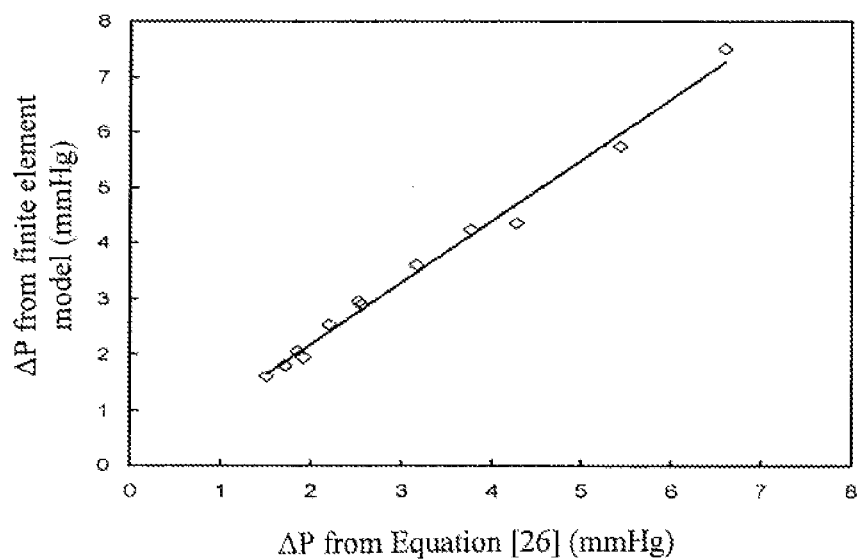
FIG. 13 shows another graph showing the validation of a finite element model according to the disclosure of the present application.

FIG. 13 shows a comparison of pressure drops across various stenoses (40, 50, 60, and 70% stenosis) with different lesion lengths (1, 2, and 3 cm) between computational results from the finite element model based on Equation [26], which itself can be used to determine FFR from an exemplary device 200 of the present disclosure as has been validated by a finite element simulation shown in FIG. 13.

Regarding data pressure and FFR measurements, if the flow and lesion geometry are accurately known, the laws of physics (conservation of mass and momentum) can accurately determine the pressure drop along the stenosis. A finite element simulation of actual blood vessel geometries was used to validate the formulation. FIG. 13 shows excellent accuracy of the physics-based equation (Equation [18]) which incorporates the measured flow and lesion geometry as compared to a finite element simulation, noting that there are no empirical parameters in this formulation, as it is strictly the geometry and flow as determined by the devices of the present disclosure and conservation laws of physics as referenced herein.

The disclosure of the present application, and in at least one embodiment, uses the premise that the injection of solution to momentarily replace the blood does not affect the normal velocity of flow through an organ. This principle has been previously validated for contrast injections where the contrast power injection only increased blood flow by less than 15%. It has been found that an injection rate of 2-4 ml/s is substantially adequate for complete replacement of blood with contrast for baseline and hyperemic flow. Power injection of contrast into a coronary artery produces a back pressure that momentarily prevents blood from entering the coronary artery. The magnitude of the generated back pressure depends on the injection rate, viscosity of injection, the ratio of vascular and aortic resistance and vessel compliance.

With the various techniques disclosed herein, and in one testing example, flow measurements were made during contrast injection and completed within three seconds after the start of contrast injection. An injection time of three seconds was adequate to ensure that only undiluted contrast material was entering the vascular bed during the flow measurement time interval. As such injections do not require a power injector, changes in flow are expected to be substantially less than 15%, which is a well accepted clinical tolerance for such a procedure.

While various embodiments of devices, systems, and methods for determining fractional flow reserve have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method for determining a flow reserve within a luminal organ, the method comprising the steps of:
   obtaining flow data comprising a flow velocity of a fluid within a luminal organ using an impedance device positioned within the luminal organ, a cross-sectional area at or near a stenosis within the luminal organ determined using conductance data obtained from the impedance device, and a pressure measurement indicative of the luminal organ, wherein the pressure measurement is determined using the flow velocity and the cross-sectional area by a data acquisition and processing system without the use of a pressure sensor; and
   determining, using the data acquisition and processing system, a flow reserve within the luminal organ at or near the stenosis using the flow velocity, the cross-sectional area, and the pressure measurement.

2. The method of claim 1, wherein the step of determining comprises determining a fractional flow reserve.

3. The method of claim 1, wherein the flow velocity is obtained using the impedance device positioned within the luminal organ at or near the stenosis.

4. The method of claim 1, wherein the flow velocity is obtained using the impedance device positioned within the luminal organ at or near the stenosis, the impedance device comprising at least two sensors separated a predetermined distance from one another.

5. The method of claim 4, wherein the flow velocity is obtained by:
   detecting a first fluid within the luminal organ using at least one of the at least two sensors, wherein the first fluid has a first parameter having a first value;
   introducing the second fluid into the luminal organ, the second fluid temporarily displacing the first fluid within the luminal organ at the site of introduction, wherein the second fluid has a second parameter having a second value, the second value differing from the first value;
   detecting the second value of the second parameter of the second fluid using the at least two sensors;
   measuring time of detection of the second value of the second parameter of the second fluid by each of the at least two sensors; and
   determining flow velocity of the second fluid within the luminal organ based upon the time of detection of the second value of the second parameter of the second fluid by each of the at least two sensors.

6. The method of claim 5, wherein the first parameter and the second parameter are conductivity, pH, temperature, or an optically-detectable substance.

7. The method of claim 1, wherein the conductance data is obtained using the impedance device when positioned within the luminal organ at or near the stenosis.

8. The method of claim 1, wherein the cross-sectional area is obtained from the conductance data obtained using the impedance device positioned within the luminal organ at or near the stenosis, the conductance data obtained using (i) the at least two sensors of the impedance device separated a predetermined distance from one another, (ii) at least one additional sensor of the impedance device, or (iii) at least one of the at least two sensors and the at least one additional sensor.

9. The method of claim 1, wherein the step of determining the flow reserve is further based upon a determination of volumetric flow between at least two sensors of an impedance device operated within the luminal organ.

10. The method of claim 1, further comprising the step of:
    diagnosing a disease based upon the determination of flow velocity within a luminal organ.

11. The method of claim 1, wherein the determination of the flow reserve is indicative of a degree of stenosis within the luminal organ.

12. A method for determining a flow reserve within a luminal organ, the method comprising the steps of:
    introducing an impedance device into a lumen of a luminal organ at or near a stenosis;
    operating the impedance device to determine a flow velocity of a fluid within the luminal organ and to obtain conductance data useful to determine a cross-sectional area within the luminal organ;
    determining a cross-sectional area within the luminal organ using the conductance data;
    determining a pressure measurement indicative of the luminal organ using a data acquisition and processing system, wherein the pressure measurement is determined using the flow velocity and the cross-sectional area without the use of a pressure sensor; and
    determining, using the data acquisition and processing system, a flow reserve at or near the stenosis using the flow velocity, the cross-sectional area, and the pressure measurement.

13. The method of claim 12, wherein the step of determining comprises determining a fractional flow reserve.

14. The method of claim 12, wherein the flow velocity is obtained by:
    detecting a first fluid within the luminal organ using at least one of at least two sensors of the impedance device, wherein the first fluid has a first parameter having a first value;
    introducing the second fluid into the luminal organ, the second fluid temporarily displacing the first fluid within the luminal organ at the site of introduction, wherein the second fluid has a second parameter having a second value, the second value differing from the first value;
    detecting the second value of the second parameter of the second fluid using the at least two sensors;
    measuring time of detection of the second value of the second parameter of the second fluid by each of the at least two sensors; and
    determining flow velocity of the second fluid within the luminal organ based upon the time of detection of the second value of the second parameter of the second fluid by each of the at least two sensors.

15. The method of claim 14, wherein the first parameter and the second parameter are conductivity, pH, temperature, or an optically-detectable substance.

16. The method of claim 12, wherein the conductance data is obtained using (i) at least two sensors of the impedance device separated a predetermined distance from one another, (ii) at least one additional sensor of the impedance device, or (iii) at least one of the at least two sensors and the at least one additional sensor.

17. The method of claim 12, wherein the step of determining the flow reserve is further based upon a determination of volumetric flow between at least two sensors of the impedance device.

18. The method of claim 12, further comprising the step of:
diagnosing a disease based upon the determination of flow velocity within a luminal organ.

19. The method of claim 12, wherein the determination of the flow reserve is indicative of a degree of stenosis within the luminal organ.

20. A system for determining a flow reserve within a luminal organ, the system comprising:
- an impedance device comprising at least two sensors separated a predetermined distance from one another, the impedance device operable to (a) determine a flow velocity of a fluid within a mammalian luminal organ; and (b) obtain conductance data within the mammalian luminal organ useful to determine a cross-sectional area of the mammalian luminal organ, when at least part of the impedance device is positioned within the mammalian luminal organ; and
- a data acquisition and processing system coupled to the impedance device, the data acquisition and processing system configured to (a) determine the cross-sectional area using the conductance data obtained from the impedance device, (b) determine a pressure measurement within the mammalian luminal organ using the flow velocity and the cross-sectional area, without the use of a pressure sensor, and (c) determine a flow reserve at or near a stenosis within the mammalian luminal organ using the cross-sectional area, the flow velocity, and the pressure measurement.

* * * * *